(12) United States Patent
Utro et al.

(10) Patent No.: US 12,283,348 B2
(45) Date of Patent: Apr. 22, 2025

(54) METHODS AND SYSTEMS FOR DETERMINING DRUG RESISTANCE USING A PRECEDENCE GRAPH

(71) Applicant: International Business Machines Corporation, Armonk, NY (US)

(72) Inventors: Filippo Utro, Pleasantville, NY (US); Laxmi Parida, Mohegan Lake, NY (US); Chaya Levovitz, New York, NY (US); Kahn Rhrissorrakrai, Woodside, NY (US)

(73) Assignee: International Business Machines Corporation, Armonk, NY (US)

( * ) Notice: Subject to any disclaimer, the term of this patent is extended or adjusted under 35 U.S.C. 154(b) by 1028 days.

(21) Appl. No.: 16/507,811

(22) Filed: Jul. 10, 2019

(65) Prior Publication Data

US 2021/0012861 A1    Jan. 14, 2021

(51) Int. Cl.
| | | |
|---|---|---|
| *G16B 40/00* | (2019.01) | |
| *G01N 33/50* | (2006.01) | |
| *G16B 5/00* | (2019.01) | |
| *G16C 20/80* | (2019.01) | |
| *G16H 10/40* | (2018.01) | |
| *G16H 15/00* | (2018.01) | |
| *G16H 70/40* | (2018.01) | |
| *G16H 80/00* | (2018.01) | |

(52) U.S. Cl.
CPC ......... *G16B 40/00* (2019.02); *G01N 33/5008* (2013.01); *G01N 33/5091* (2013.01); *G16B 5/00* (2019.02); *G16C 20/80* (2019.02); *G16H 10/40* (2018.01); *G16H 15/00* (2018.01); *G16H 70/40* (2018.01); *G16H 80/00* (2018.01)

(58) Field of Classification Search
CPC ........... G16B 40/00; G16B 5/00; G16C 20/80
USPC ........................................................ 702/19
See application file for complete search history.

(56) References Cited

U.S. PATENT DOCUMENTS

| | | |
|---|---|---|
| 6,165,709 A | 12/2000 | Friend et al. |
| 7,751,988 B2 | 7/2010 | Kita et al. |
| 2003/0131015 A1 | 7/2003 | Chen |
| 2015/0320755 A1 | 11/2015 | Kutok et al. |
| 2017/0286508 A1 | 10/2017 | Gupta et al. |
| 2017/0316147 A1 | 11/2017 | Gao et al. |
| 2018/0218270 A1 | 8/2018 | Manikonda et al. |

OTHER PUBLICATIONS

Reiter, Johannes G., et al. "Reconstructing metastatic seeding patterns of human cancers." Nature communications 8.1 (2017): 1-10.*
Beltrame, L., et al. "Profiling cancer gene mutations in longitudinal epithelial ovarian cancer biopsies by targeted next-generation sequencing: a retrospective study." Annals of Oncology 26.7 (2015): 1363-1371.*
Roncolato, Felicia T., et al. "Reducing uncertainty: predictors of stopping chemotherapy early and shortened survival time in platinum resistant/refractory ovarian cancer—the GCIG symptom benefit study." The Oncologist 22.9 (2017): 1117-1124.*
Reiter, Johannes G., et al. "Reconstructing metastatic seeding patterns of human cancers." Nature communications 8.1 (2017): 1-10. (Year: 2017).*
Beltrame, L., et al. "Profiling cancer gene mutations in longitudinal epithelial ovarian cancer biopsies by targeted next-generation sequencing: a retrospective study." Annals of Oncology 26.7 (2015): 1363-1371. (Year: 2015).*
Chang, Yoosup, et al. "Cancer drug response profile scan (CDRscan): a deep learning model that predicts drug effectiveness from cancer genomic signature." Scientific reports 8.1 (2018): 8857. (Year: 2018).*
Roncolato, Felicia T., et al. "Reducing uncertainty: predictors of stopping chemotherapy early and shortened survival time in platinum resistant/refractory ovarian cancer—the GCIG symptom benefit study." The Oncologist 22.9 (2017): 1117-1124. (Year: 2017).*
"Snpeff & SnpSift." SnpEff and SnpSift, http://pcingola.github.io/SnpEff/. (Year: 2022).*
Jeselsohn, Rinath, et al. "ESR1 mutations—a mechanism for acquired endocrine resistance in breast cancer." Nature reviews Clinical oncology 12.10 (2015): 573-583. (Year: 2015).*
Caravagna, Giulio, et al. "Algorithmic methods to infer the evolutionary trajectories in cancer progression." Proceedings of the National Academy of Sciences 113.28 (2016): E4025-E4034. (Year: 2016).*
Zeng, Tao, et al. "Prediction of dynamical drug sensitivity and resistance by module network rewiring-analysis based on transcriptional profiling." Drug Resistance Updates 17.3 (2014): 64-76. (Year: 2014).*
Forbes, S. A. et al. Cosmic: somatic cancer genetics at high-resolution. Nucleic Acids Res. 45, 777-83 (2017).*
R. Condorelli et al., "Polyclonal RB1 Mutations and Acquired Resistance to CDK 4/6 Inhibitors in Patients with Metastatic Breast Cancer," Annals of Oncology, Mar. 1, 2018, pp. 640-645, vol. 29, No. 3.
B. O'Leary et al., "The Genetic Landscape and Clonal Evolution of Breast Cancer Resistance to Palbociclib Plus Fulvestrant in the Paloma-3 Trial," Cancer Discovery, Nov. 2018, pp. 1390-1403, vol. 8, No. 11.
T. Cheng et al., "Large-Scale Prediction of Drug-Target Interaction: a Data-Centric Review," The AAPS Journal, Sep. 2017, pp. 1264-1275, vol. 19, No. 5.

* cited by examiner

*Primary Examiner* — G. Steven Vanni
(74) *Attorney, Agent, or Firm* — Kristofer Haggerty; Ryan, Mason & Lewis, LLP

(57) ABSTRACT

A computer-implemented method is disclosed which includes receiving biological sample information from one or more subjects at a first time period. The method further includes receiving biological sample information from the one or more subjects at a second time period. The method further includes comparing the biological sample information at the second time period with the biological sample information at the first time period. The method further includes generating a precedence graph based on results of the comparison. The method further includes determining one or more actions based on the precedence graph.

15 Claims, 5 Drawing Sheets

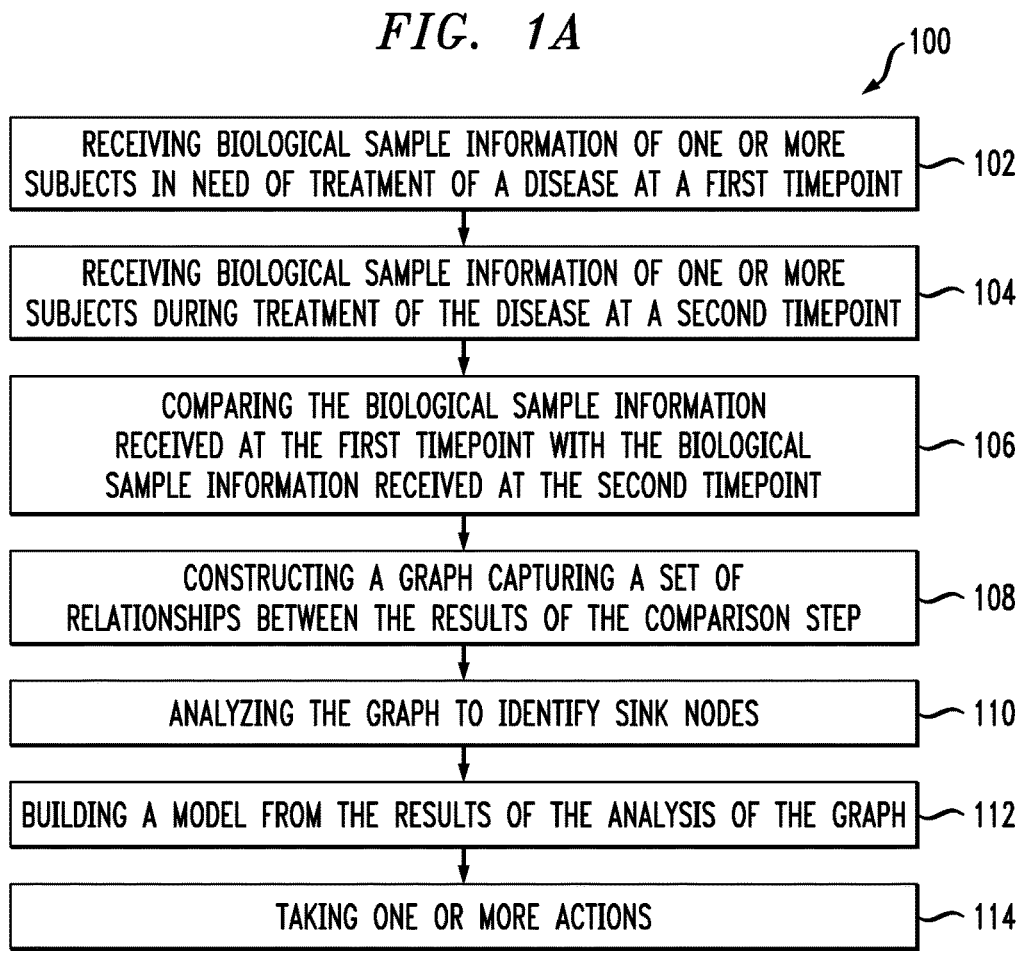
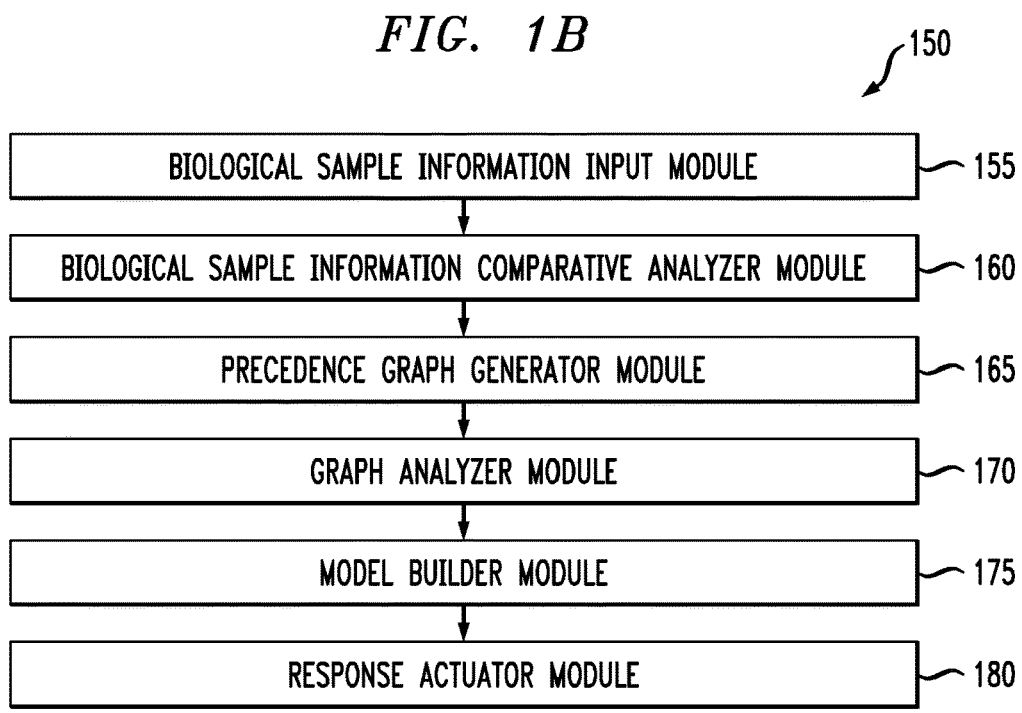

METHODS AND SYSTEMS FOR DETERMINING DRUG RESISTANCE USING A PRECEDENCE GRAPH

BACKGROUND

Diseases such as cancer involve the abnormal growths of cells. For example, cancer cells rapidly reproduce despite restriction of space, nutrients shared by other cells, or signals sent from the body to stop reproduction. Cancer cells are often shaped differently from healthy cells, do not function properly, and can spread into many areas of the body. Abnormal growths of tissue, called tumours, are clusters of cells that are capable of growing and dividing uncontrollably. Tumours can be benign (noncancerous) or malignant (cancerous). Malignant cancers can be both locally invasive and metastatic.

Breast cancer is an example of a common cancer and is a complex disease due to its morphological and biological heterogeneity, its tendency to acquire chemo-resistance and the existence of several molecular mechanisms underline its pathogenesis. Half of women who receive loco-regional treatment for breast cancer will never relapse, whereas the other half will eventually die from metastatic disease.

Treatment for diseases such as cancer can vary depending on the stage of progression of the cancer. There can be a relatively slow or rapid acquisition of resistance to cancer drugs which remains a key obstacle to successful cancer therapy. Substantial efforts to elucidate the molecular basis for such drug resistance have revealed a variety of mechanisms, including drug efflux, acquisition of drug binding-deficient mutants of the target, engagement of alternative survival pathways, and epigenetic alterations. Such mechanisms are generally believed to reflect the existence of resistance-conferring genetic alterations within a tumor cell population that is selected during drug treatment.

SUMMARY

Embodiments described herein provide methods for determining drug resistance from one or more subjects' time-course biological profiles using precedence graphs. For example, in one exemplary embodiment, a computer-implemented method comprises receiving biological sample information from one or more subjects at a first time period. The method further comprises receiving biological sample information from the one or more subjects at a second time period. The method further comprises comparing the biological sample information at the second time period with the biological sample information at the first time period. The method further comprises generating a precedence graph based on results of the comparison. The method further comprises determining one or more actions based on the precedence graph. The steps of the method are performed in accordance with a processor and a memory.

Another exemplary embodiment includes an article of manufacture to determine drug resistance from one or more subjects' time-course biological profiles using precedence graphs. The article of manufacture includes a computer-readable storage medium for storing computer-readable program code which, when executed, causes a computer to receive biological sample information from one or more subjects at a first time period. The computer is further caused to receive biological sample information from the one or more subjects at a second time period. The computer is further caused to compare the biological sample information at the second time period with the biological sample information at the first time period. The computer is further caused to generate a precedence graph based on results of the comparison. The computer is further caused to determine one or more actions based on the precedence graph.

Another exemplary embodiment includes a system to determine drug resistance from one or more subjects' time-course biological profiles using precedence graphs which comprises: a memory and a processor. The processor is operatively coupled to the memory and configured to implement the step of receiving biological sample information from one or more subjects at a first time period. The processor is operatively coupled to the memory and configured to implement the step of receiving biological sample information from the one or more subjects at a second time period. The processor is operatively coupled to the memory and configured to implement the step of comparing the biological sample information at the second time period with the biological sample information at the first time period. The processor is operatively coupled to the memory and configured to implement the step of generating a precedence graph based on results of the comparison. The method further comprises determining one or more actions based on the precedence graph.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 1A shows a flow diagram illustrating a process for determining drug resistance from one or more subjects' time-course molecular profiles, according to an embodiment of the invention.

FIG. 1B shows a system diagram illustrating a system for determining drug resistance from one or more subjects' time-course molecular profiles, according to an embodiment of the present invention.

DETAILED DESCRIPTION

Figure 2A:
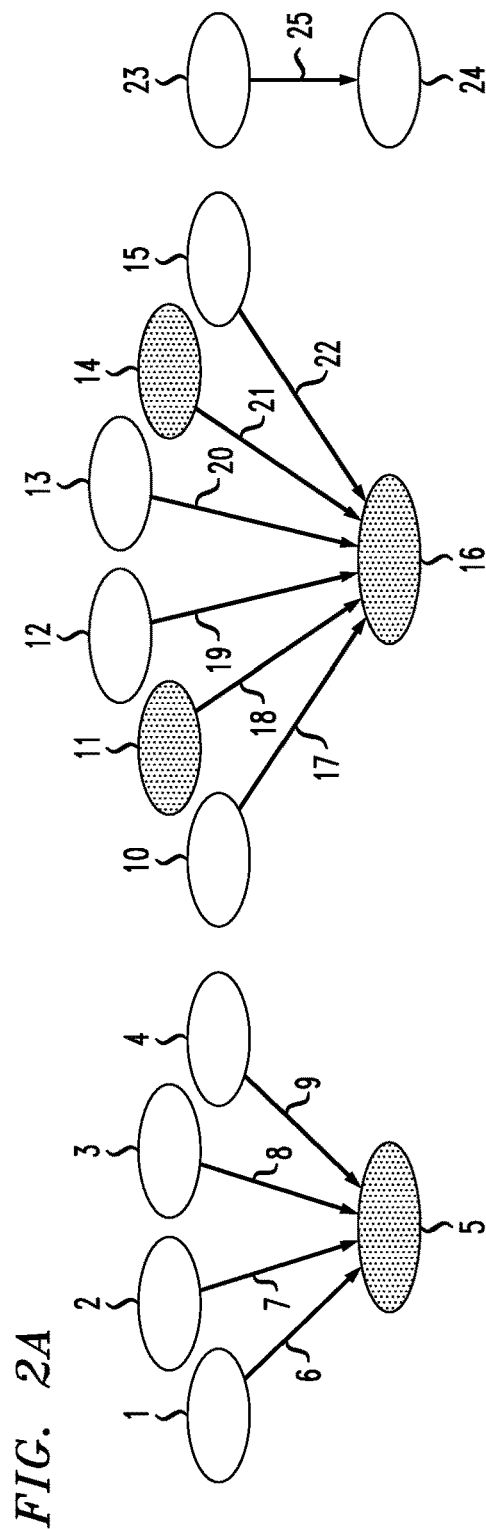
FIG. 2A depicts an exemplary precedence graph, according to an embodiment of the present invention.

Embodiments of the present invention will now be described in further detail with regard to methods and systems for determining, for example, drug resistance from one or more subjects' time-course genomic profiles, thereby leading to more beneficial outcomes for disease treatment. As discussed above, genetic alterations within a tumor cell population can lead to the existence of drug resistance during treatment. However, identification of genetic alterations that impact a drug(s) response remains challenging since the alterations are hidden in large complex sequencing datasets. In addition, the identification of suitable combination therapies to improve response and decrease resistance is a problem to be solved in the treatment of, for example, cancer patients. The embodiments of the present invention therefore introduce a method and system for identifying genetic alterations underlying a drug(s) response (e.g., resistance) using time-course data that are otherwise unknown. Other embodiments of the present invention include (a) prediction of potential future genomic alterations based on the background of the subject or similar subjects; and (b) simulation of a subject's genomic alteration profile.

As further detailed herein, one or more embodiments of the present invention include the identification of suitable combination drug therapies to improve response to the drug therapy and decrease drug resistance in the treatment of a disease, e.g., cancer patients. Representative examples of combination treatments that can be identified using precedence graphs include:

In diffuse large B-cell lymphoma, expression of BCL-2 is associated with poor prognosis and a decreased efficacy of chemotherapy. Clinical trials found that the addition of rituximab to the standard therapy (CHOP—cyclophosphamide, doxorubicin, vincristine, and prednisone) had higher response rates and 2-year overall survival and event-free survival rates.

For recurrent or persistent ovarian cancers or high-grade stromal tumors, Bevacizumab (VEGF inhibitor), PARP inhibitors, and/or hormone therapies are combined with a chemotherapy regimen, as these cancers can develop resistance to traditional chemotherapy.

Noscapine (a benzylisoquinoline alkaloid) has been used in clinical trials in low concentrations to sensitize triple negative breast cancer to docetaxel, a traditional chemotherapeutic drug. It was found that Noscapine inhibited the proliferation of resistant and non-resistant breast cancer cells. The combination of Noscapine and docetaxel showed significant reduction in tumor volume compared to either drug alone. The combination was found to downregulate anti-apoptotic proteins, as well as multidrug resistance proteins.

Paclitaxel is a first-line therapy for breast, lung, and ovarian cancers. However, successful therapy is frequently hindered by the development of resistance to paclitaxel through elevated expression of prohibitin1 (PHB1) and GSTπ. Small interfering RNAs (siRNAs) have been successfully used to silence PHB1 and GSTπ to partially increase sensitivity to paclitaxel via the activation of intrinsic apoptotic pathways.

In one exemplary embodiment, a system and method described herein can be used, for example, to validate a known resistance mechanism while discovering new mechanisms with the same or increased level of mutational convergence. For example, mutations in the RB1 gene has have been discovered as a mechanism of resistance in CDK4/6 treated metastatic breast cancer. Yet another example is the NACA gene which has an increased convergence as compared to RB1 and might be another mechanism of drug resistance in metastatic breast cancer. In another exemplary embodiment, a system and method described herein can be used to determine the genetic context of a subject and the pattern of changes over time to identify drug targets and combinations of drug targets, e.g., in the case of the development of resistance. In yet another exemplary embodiment, a system and method described herein can be used to determine the pattern of genetic change over time, and not just the presence or absence of alterations, in order to identify drug targets and potential effective combination drug therapies.

The terms "subject", "patient", "mammal", "individual", and the like are used interchangeably herein, and refer to any animal, or cells thereof whether in vitro or in situ, amenable to the methods described herein. In certain non-limiting embodiments, the subject, patient or individual is a human.

The term "biological sample" is used herein in its broadest sense. A sample may be of any biological tissue or fluid from which biomarkers of the present invention may be detected, extracted, isolated, characterized or measured. Examples of such samples include but are not limited to blood, lymph, urine, gynecological fluids, biopsies, amniotic fluid and smears. Samples that are liquid in nature are referred to herein as "bodily fluids". Biological samples may be obtained from a patient by a variety of techniques including, for example, by scraping or swabbing an area or by using a needle to aspirate bodily fluids. Methods for collecting various biological samples are well known in the art. Frequently, a sample will be a "clinical sample", i.e., a sample derived from a patient. Such samples include, but are not limited to, bodily fluids which contain cells, e.g., blood (e.g., whole blood, serum or plasma), urine, saliva, tissue or fine needle biopsy samples, and archival samples with known diagnosis, treatment and/or outcome history. Biological samples also include tissues, such as, frozen sections taken for histological purposes. The sample also encompasses any material derived by processing a biological sample. Derived materials include, but are not limited to, cells (or their progeny) isolated from the sample, proteins or nucleic acid molecules extracted from the sample. Processing of a biological sample may involve one or more of: filtration, distillation, extraction, concentration, inactivation of interfering components, addition of reagents, and the like.

The term "disease" as used herein shall be understood to mean any phenotype or phenotypic trait of concern including, by way of example, a disease or disease state, and a predisposition or susceptibility to a disease. Illustrative and non-limiting examples of disease states include cancer, HIV, leukemia, high cholesterol levels, heart failure, hypertension, diabetes, glucose intolerance, etc.

The terms "therapy", "treating" and "treatment" of a disease, state, disorder or condition as used herein shall be understood to mean: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The term "drug" as used herein shall be understood to mean a therapeutic used in the treatment or prevention of a disease. For example, an anti-cancer agent can be used to treat cancer. An anti-cancer agent refers to a composition (e.g., compound, drug, antagonist, inhibitor, modulator) having antineoplastic properties or the ability to inhibit the growth or proliferation of cells, and includes, for example, antibodies, small molecules, and large molecules or combinations thereof. Representative examples of anti-cancer agents include any known or later-discovered drug for any and all such applications.

FIGS. 1A and 1B shows a process flow and system for determining drug resistance from one or more subjects' time-course molecular profiles according to an illustrative embodiment of the invention. The systems and methods described herein may be implemented in hardware, software (e.g., firmware), or a combination thereof. In some embodiments, the methods described may be implemented, at least in part, in hardware and may be part of a microprocessor of a special or general-purpose computer system, such as a personal computer, workstation, minicomputer, or mainframe computer. Referring to FIG. 1A, the process flow 100 includes, in step 102, receiving biological sample information from one or more subjects in need of treatment of a disease at a first timepoint. In other words, the biological sample information of the one or more subjects is received when the subjects are in need of treatment of a disease. Accordingly, by way of example, biological sample information can be genomic information including, by not limited to, information relating to chromosome structure, DNA or RNA sequence, length of a specific gene or region, gene expression, such as mRNA or transcription levels, identification of one or more single nucleotide polymorphisms (SNPs), and/or any other information relating to a subject's genetic makeup. Alternatively, or additionally, the biological sample information can comprise a record of actual DNA base sequences at one or more regions within a genome. Still further, the biological sample information can comprise a record of variation between a specified sequence on a chromosome of that subject compared to a reference sequence, indicating whether, and to what extent, there is a variation at identical positions within the sequence. In one embodiment, the one or more subjects can include 1 or more subjects, or 5 or more subjects, or 10 or more subjects, or 100 or more subjects or 1,000 or more subjects, etc. In one embodiment, the plurality of subjects can include 50,000 or less subjects, or 25,000 or less subjects, or 10,000 or less subjects, or 5,000 or less subjects, etc. Methods for determining the biological sample information are within the purview of one skilled in the art.

The process flow 100 further includes, in step 104, receiving biological sample information of the plurality of subjects at a second timepoint. The biological sample information received at the second timepoint includes information directed to the genomic alteration of the biological sample. As one skilled in the art will understand, genomic alteration of the biological sample includes alterations and their effects observed include, but are not limited to, DNA (including CNV), RNA, proteome, nucleosome pattering, etc. For example, as discussed above, a biological sample can mutate over the course of treatment to form the RB1 gene. For example, the second time period can be at a time during treatment of a disease. Treatment of the disease is by way of delivering a therapeutically effective amount of one or more drugs for the specific disease being treated. Thus, for example, a subject diagnosed with breast cancer will begin treatment with one or more of the foregoing anti-cancer agents for a predetermined time period. In another embodiment, the second time period can be at a time to determine if an immune response from the subject has occurred to a condition in the body. For example, a condition in the body may be treated by an immune response. Accordingly, a second time period can be at a time to determine if any genomic alterations of the biological sample have occurred due to the immune response within the body.

In general, the second time point is defined by the lapse of time from the initial time point whereby some form of treatment is given or an immune response may or may not have occurred in between these two points. If there are multiple samples taken after the initial timepoint or "before treatment" timepoint then the second timepoint is chosen to be the sample closest to the "end" of the given treatment course or immune response thus maximizing the opportunity to capture any possible change that may occur as a result thereof. However, a change in the biological sample information is not necessary for the second time point as it may be the case that there is no change.

Accordingly, in one embodiment, the second timepoint is a time sufficient to deliver the one or more drugs to the subject being treated such that administration of the drug provides an observable result. This second time point can be any time point taken after start of the treatment whereby changes in the biological sample could be observed and the difference in time between the first and second timepoint may be in part dependent upon the data type being sampled whereby changes in the levels of, for example, RNA, can occur more quickly than changes in the DNA. Methods for determining the biological sample information at the second timepoint are within the purview of one skilled in the art. In another embodiment, the second timepoint is a time sufficient for the subject's immune response provides an observable result or no observable result.

The process flow 100 further includes, in step 106, comparing the biological sample information received at the first timepoint with the biological sample information received at the second timepoint. The comparison is carried out to determine if any new genomic alteration (e.g. mutation) has occurred in the biological samples over the course of treatment. This occurrence can be defined in multiple ways, in one embodiment a pair of alterations, if the two are in the same clone (or sub-clone), can be defined as one alteration present in first timepoint and another present in the second but not the first time point. A clone is a group of identical cells that share a common origin, i.e. they are derived from the same cell. An empirical way to define clone is based on the infinite site assumption, i.e. mutations with similar variant allele frequency (VAF) or cancer cell fraction (CCF) belong to the same sub-clone.

The process flow 100 further includes, in step 108, constructing a graph capturing a set of relationships from the results of the comparison step. For example, as shown in FIG. 2A, a precedence graph can be generated by using frequencies of related pairs to identify those that meet a significance threshold given overall distribution of frequencies. A significance threshold can be defined in multiple ways and one embodiment is to take all pairs occurring at a frequency above two standard deviations from the mean of all pair frequencies. In another embodiment, the significance threshold can be based on k-way interactions. As illustrated in FIG. 2A, related nodes 1 to 4 show a similar genomic alteration in sink node 5 having edges 6-9. FIG. 2A further illustrates related nodes 10-15 showing a similar genomic alteration in sink node 16 having edges 17-22. Finally, node 23 has no related nodes and contains a genomic alteration in sink node 24 with edge 25. The edges are direct relationships between pairs of genes indicating precedence of mutated status. An edge can be weighted (e.g., by significance value as these could contribute to the overall significance of the "sink").

The process flow 100 further includes, in step 110, applying a graph analysis technique to identify, for example, sink nodes, that may indicate which genomic alterations tend to arise over the course of treatment of a particular drug or drug combination that would be potential targets for further treatment and/or to identify multiple sink nodes that can guide the development of combination therapies. The graph analysis technique can also be applied to identify, for example, sink nodes, that may indicate which genomic alterations tend to arise from the subject's immune response.

Figure 2B:
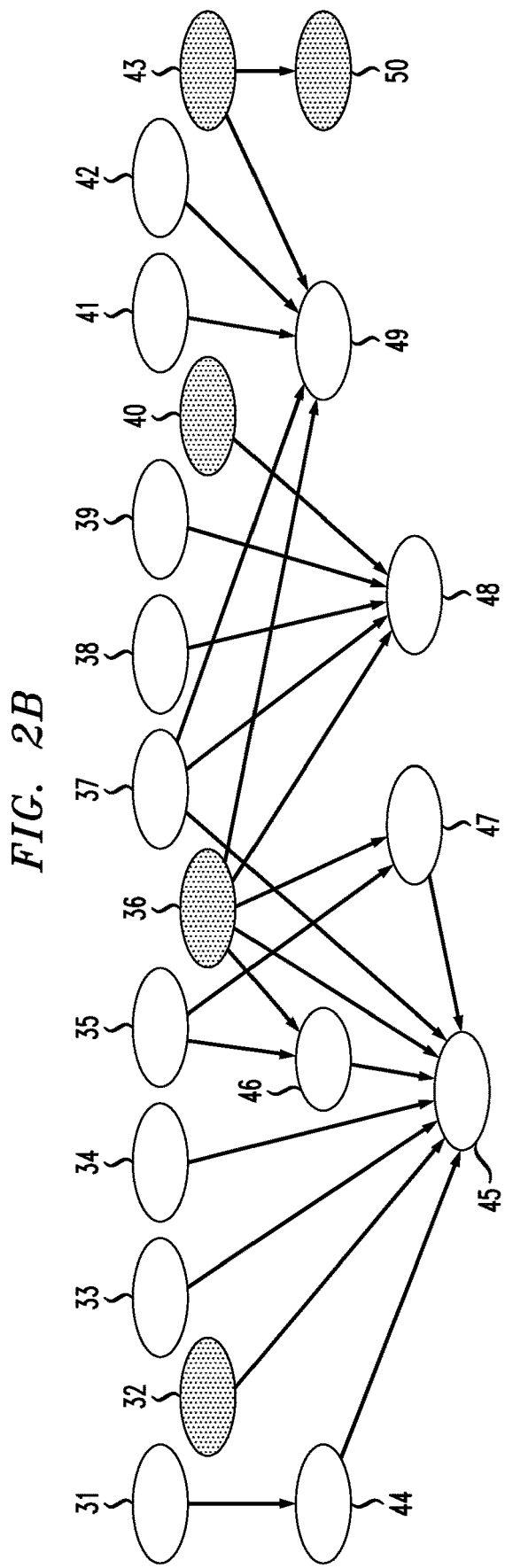
FIG. 2B depicts an exemplary precedence graph, according to an embodiment of the invention.

In one illustrative embodiment, as shown in FIG. 2B, when looking at a plurality of subjects having a gene denoted by nodes 31-43 and being treated with drugs A and B, it is first seen that related nodes 32-34, 36 and 37 contained a similar genomic alteration in sink node 15. In addition, node 31 has a genomic alteration in sink node 44, along with node 35 which has a genomic alteration in sink nodes 46 and 47, which were related nodes by having a genomic alteration in sink node 45. Next, it can be seen that related nodes 36-40 contained a similar genomic alteration in sink node 18. Next, it can further be seen that related nodes 36, 37 and 41-43 contained a similar genomic alteration in sink node 49. Finally, unrelated nodes 31 and 43 contained dissimilar genomic alterations in respective sink nodes 44 and 50. FIG. 2B further shows that nodes 35-37 and 43 had multiple edges. Thus, with the identified sink nodes, it is then possible to use them as guidance for treatment by identifying patterns of paired dependent mutations, i.e., sink nodes, over the course of treatment to associate subjects with shared subject-specific mechanisms of resistance. An example is a new patient walking in the clinic, and when the genomic profile at the first time point found a genomic alteration in the graph, the clinician can use the knowledge in the graph to predict that the treatment will induce a new set of genomic alterations and preemptively consider a different treatment or some drug combination.

Alternatively, the graph analysis technique can include the study of source nodes or hubs to identify possible actions (e.g., drug-targets). Source nodes are those nodes with exclusively outgoing edges. Hubs are nodes with a relatively high number of edges. Graph analysis techniques may include, but are not limited to, network flow or diffusion analysis whereby a signal is propagated from the source nodes through a network as a function of the edge degree, weight or other features of the graph. Clustering may also be applied to the graph to identify groupings of nodes that are more closely interacting and thus may represent larger functional processes. Hubs may serve to represent potential actionable items as they are more necessary for signal flow through the network. Hubs with primarily incoming edges may represent alterations that are being selected for in the tumor in response to the selective pressure being applied to the tumor.

The process flow 100 further includes, in step 112, building a model from the results of the analysis of the graph. For example, models based on historical data of past performance for each biological sample information and treatment thereof can be built, e.g., the model can be built with the respective genes, their alterations and response to the drug treatment. In this manner, identification of post treatment mutational convergence (e.g., sinks with several edges) can suggest a resistance mechanism emerging in response to a given treatment across a patient cohort. In one embodiment, creating the model herein comprises using a statistical modeling process. For example, the model may be created via a machine learning process, a Gaussian process, etc. See, e.g., Rasmussen et al., "Gaussian Processes for Machine Learning", Massachusetts Institute of Technology, 2006.

The process flow 100 further includes, in step 114, taking one or more actions. For example, when a new patient comes in for treatment, and the biological sample information is received at the first time period prior to treatment, the patient's profile can be compared with the model built from the precedence graph to determine probabilities of which alterations are likely to develop given their profile based upon the calculated frequencies and models built. From the probabilities of developed alterations, the appropriate combination of drug treatments that target these alterations can be used. In one embodiment, the one or more actions can include stopping treatment of the disease with the one or more drugs. In another embodiment, the one or more actions can include altering treatment of the disease with the one or more other drugs. In another embodiment, the one or more actions can include altering treatment of the disease with the one or more additional drugs.

If desired, biological sample information can be received at additional predetermined time periods during treatment to determine if any additional genomic alterations have occurred such that the dosage of the drug treatment or the drug treatment itself can be changed or the drug treatment can be ceased as it is no longer effective. This information can then be included to further build the model. In another embodiment, biological sample information can be received at additional predetermined time periods to determine if the subject's immune response is being effective.

An illustrative system for implementing the process flow illustrated in FIG. 1A is shown in FIG. 1B. With reference to FIG. 1B, system 150 includes at least a biological sample information input module 155, a biological sample information comparative analyzer module 160, a precedence graph generator module 165, a graph analyzer module 170, a model builder module 175 and a response actuator module 180. In general, biological sample information input module 155 carries out receiving biological sample information such as, for example, steps 102 and 104 in the process flow 100. Biological sample information comparative analyzer module 160 carries out comparing the biological sample information received at one timepoint with the biological sample information received at another timepoint such as, for example, step 106 in the process flow 100. Precedence graph generator module 165 generates a precedence graph such as, for example, step 108 of process flow 100. Graph analyzer module 170 analyzes the precedence graph such as, for example, step 110 of process flow 100. Model builder module 175 builds a model based on the results of the graph analyzer such as, for example, step 112 of process flow 100. Response actuator module 180 determines one or more actions to be taken in response to the results of analyzing the graph and/or building the model such as, for example, step 114 of process flow 100.

Figure 3:
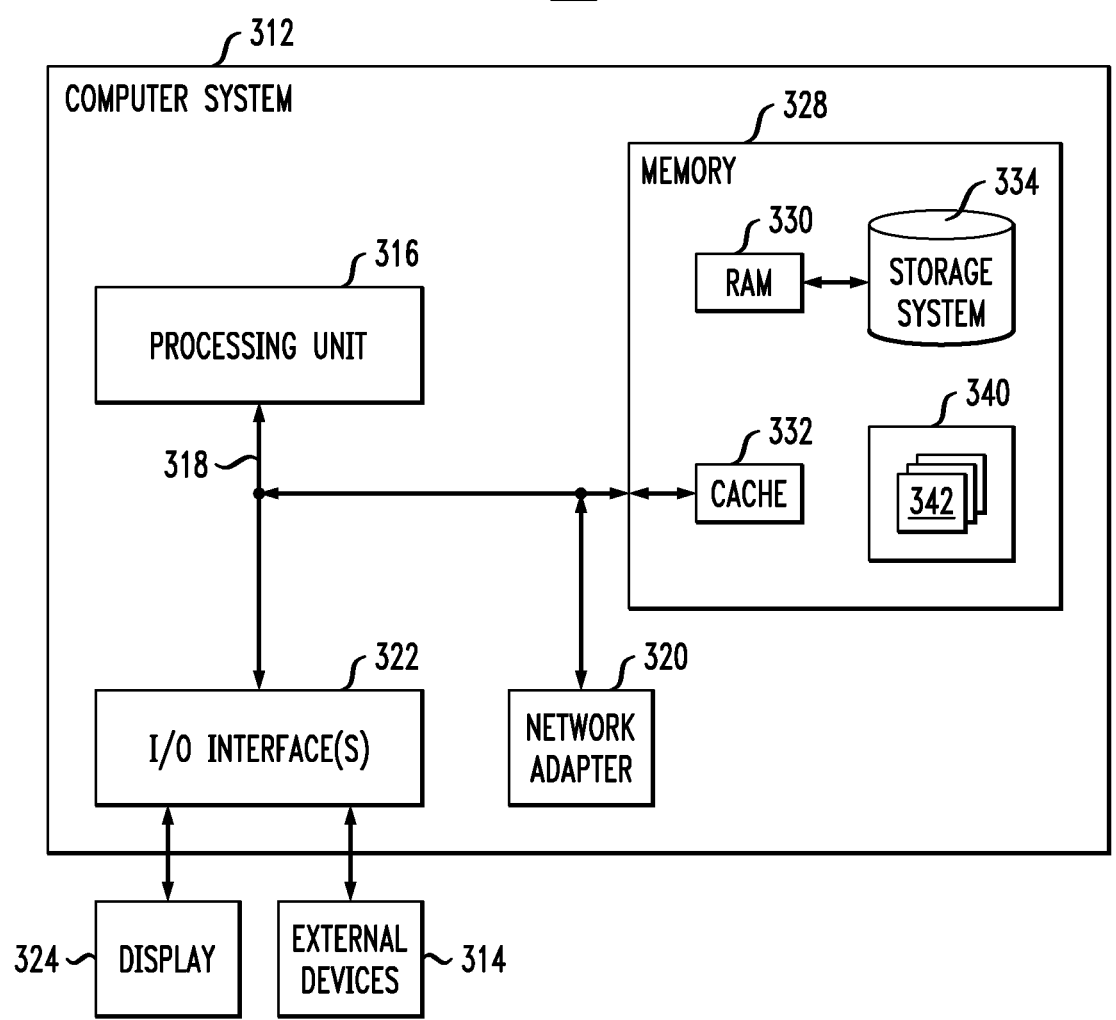
FIG. 3 depicts a computer system in accordance with which one or more components/steps or techniques of the invention may be implemented according to an embodiment of the invention.

One or more embodiments of the process and system herein can make use of software running on a computer or workstation. With reference to FIG. 3, in a computing node 310 there is a system/server 312, which is operational with numerous other general purpose or special purpose computing system environments or configurations. Examples of well-known computing systems, environments, and/or configurations that may be suitable for use with system/server 312 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

System/server 312 may be described in the general context of computer system executable instructions, such as program modules, being executed by a computer system. Generally, program modules may include routines, programs, objects, components, logic, data structures, and so on that perform particular tasks or implement particular abstract data types. System/server 312 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, system/server 312 is shown in the form of a computing device. The components of system/server 312 may include, but are not limited to, one or more processors or processing units 316, system memory 328, and bus 318 that couples various system components including system memory 328 to processor 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

System/server 312 typically includes a variety of computer system readable media. Such media may be any available media that is accessible by system/server 312, and it includes both volatile and non-volatile media, removable and non-removable media.

The system memory 328 can include computer system readable media in the form of volatile memory, such as random access memory (RAM) 330 and/or cache memory 332. System/server 312 may further include other removable/non-removable, volatile/nonvolatile computer system storage media. By way of example only, storage system 334 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 318 by one or more data media interfaces.

As depicted and described herein, memory 328 may include at least one program product having a set (e.g., at least one) of program modules that are configured to carry out the functions of embodiments of the invention. A program/utility 340, having a set (at least one) of program modules 342, may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the invention as described herein.

System/server 312 may also communicate with one or more external devices 314 such as a keyboard, a pointing device, an external data storage device (e.g., a USB drive), display 324, one or more devices that enable a user to interact with system/server 312, and/or any devices (e.g., network card, modem, etc.) that enable system/server 312 to communicate with one or more other computing devices. Such communication can occur via I/O interfaces 322. Still yet, system/server 312 can communicate with one or more networks such as a LAN, a general WAN, and/or a public network (e.g., the Internet) via network adapter 320. As depicted, network adapter 320 communicates with the other components of system/server 312 via bus 318. It should be understood that although not shown, other hardware and/or software components could be used in conjunction with system/server 312. Examples include, but are not limited to, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
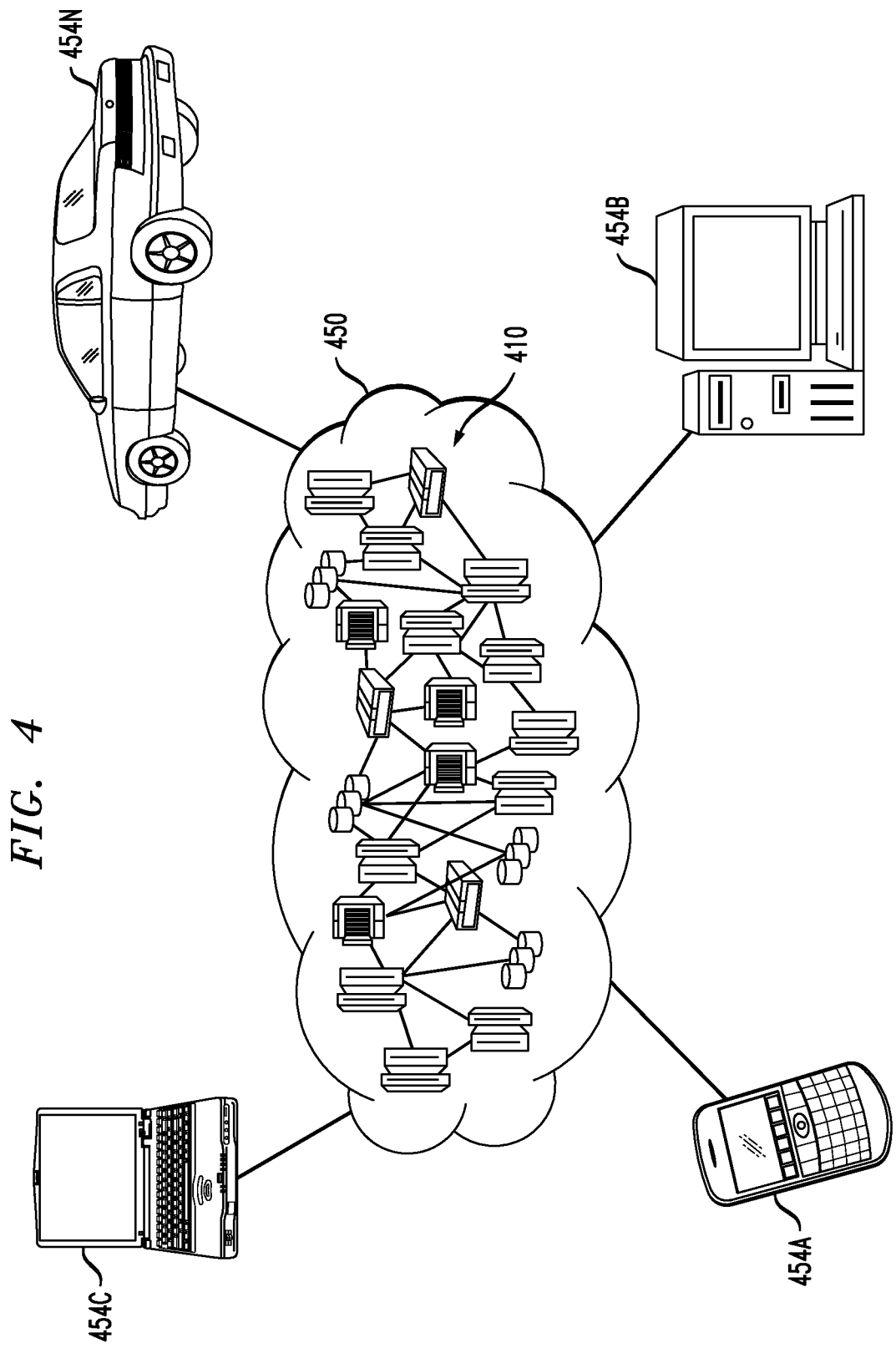
FIG. 4 depicts a cloud computing environment according to an embodiment of the invention.

Referring now to FIG. 4, illustrative cloud computing environment 450 is depicted. As shown, cloud computing environment 450 includes one or more cloud computing nodes 410 with which local computing devices used by cloud consumers, such as, for example, personal digital assistant (PDA) or cellular telephone 454A, desktop computer 454B, laptop computer 454C, and/or automobile computer system 454N may communicate. Nodes 410 may communicate with one another. They may be grouped (not shown) physically or virtually, in one or more networks, such as Private, Community, Public, or Hybrid clouds as described hereinabove, or a combination thereof. This allows cloud computing environment 450 to offer infrastructure, platforms and/or software as services for which a cloud consumer does not need to maintain resources on a local computing device. It is understood that the types of computing devices 454A-N shown in FIG. 4 are intended to be illustrative only and that computing nodes 410 and cloud computing environment 450 can communicate with any type of computerized device over any type of network and/or network addressable connection (e.g., using a web browser).

Figure 5:
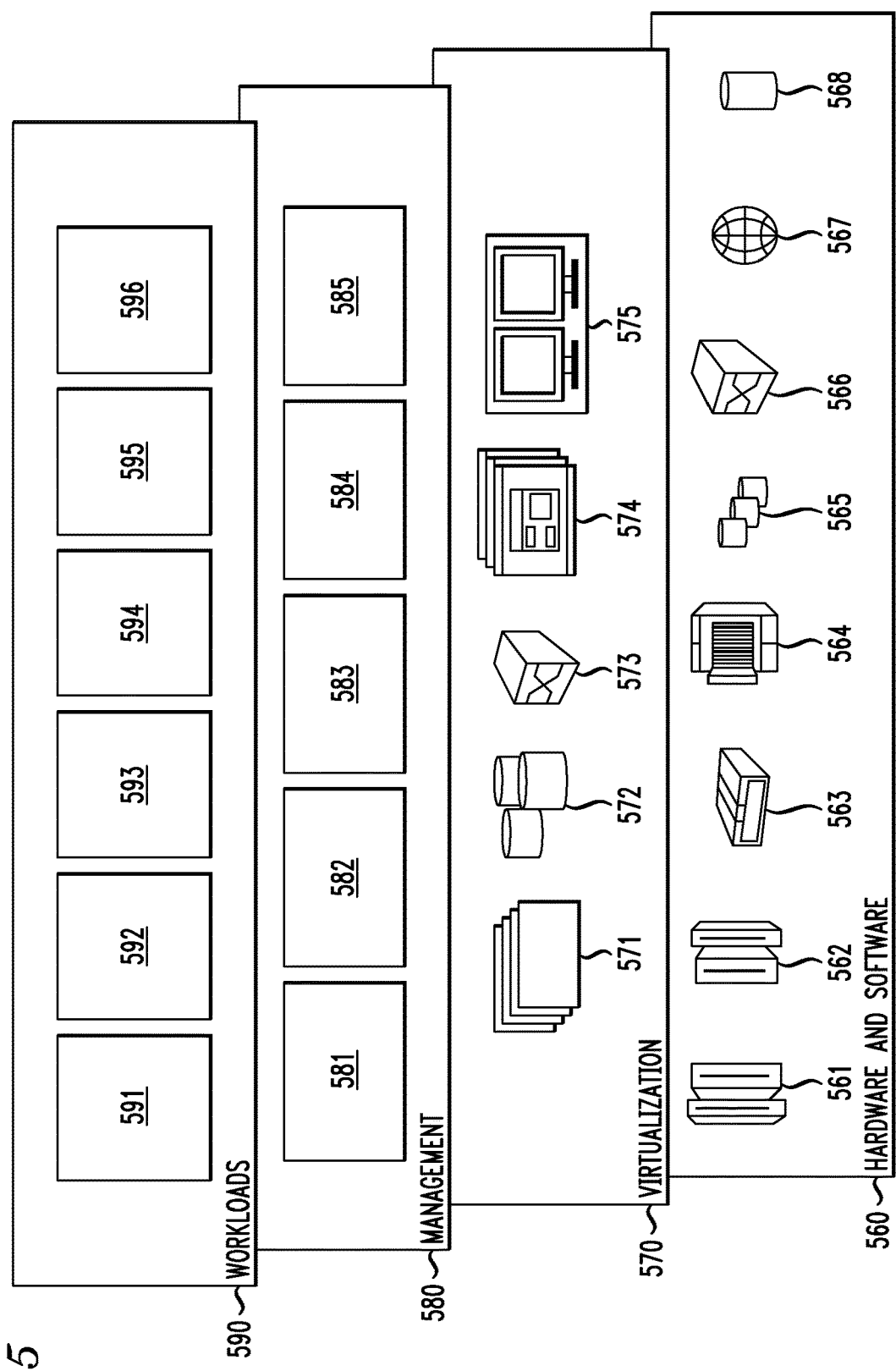
FIG. 5 depicts abstraction model layers according to an embodiment of the present invention.

Referring now to FIG. 5, a set of functional abstraction layers provided by cloud computing environment 450 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 474; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provide pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and drug resistance system 596 as described above.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although illustrative embodiments have been described herein with reference to the accompanying drawings, it is to be understood that the invention is not limited to those precise embodiments, and that various other changes and modifications may be made by one skilled in art without departing from the scope or spirit of the invention.

What is claimed is:
1. A computer-implemented method, the method comprising the steps of:
  receiving, from a biological sample information input module associated with a network, biological sample information comprising genomic information from a plurality of subjects at a first time period, wherein the first time period is before a first drug treatment of cancer;
  receiving, from the biological sample information input module associated with the network, biological sample information from the plurality of subjects at a second time period, wherein the second time period is during the first drug treatment with one or more drugs;
  comparing, utilizing a biological sample information comparative analyzer module associated with the network, the biological sample information at the second time period with the biological sample information at the first time period;
  generating, from a precedence graph generator module associated with the network, a precedence graph based on results of the comparison, wherein the precedence graph is generated by using frequencies of related pairs from a graph capturing a set of relationships from the comparing to identify those that meet a significance threshold from a given overall distribution of frequencies;

analyzing, utilizing the precedence graph generator module associated with the network, the precedence graph to determine if the biological sample information at the second time period comprises genomic alteration information of the biological sample for each of the plurality of subjects;

building, from a model builder module associated with the network, a model based on the analyzing the precedence graph utilizing a machine learning process;

implementing, based on a response actuator module associated with the network, a second drug treatment of cancer to one or more given subjects of the plurality of subjects based in part on the model;

comparing, utilizing the biological sample information comparative analyzer module associated with the network, biological sample information of a biological sample of another given subject different from the one or more given subjects of the plurality of subjects taken before a third drug treatment of cancer with the model based on analyzing the precedence graph to determine one or more probabilities of development of an alteration of the biological sample of the other given subject different from the one or more given subjects of the plurality of subjects; and based on the one or more probabilities of development of an alteration of the biological sample, implementing, based on the response actuator module associated with the network, the third drug treatment to the other given subject that target the alteration;

wherein building, from the model builder module associated with the network, a model based on the analyzing the precedence graph utilizing a machine learning process, further comprises:

storing historical data of past performance for each biological sample information;

storing genomic alterations associated with a given drug treatment different from the first drug treatment, the second drug treatment and the third drug treatment of a particular drug or a drug combination that are potential targets for further drug treatment; and creating a set of identified post-treatment mutational convergences associated with a resistance mechanism in response to the given drug treatment;

wherein implementing, based on the response actuator module associated with the network, the second drug treatment to the one or more given subjects of the plurality of subjects based in part on the model comprises identifying one or more other drugs different than the one or more drugs of the first drug treatment to improve response to the second drug treatment and decrease drug resistance in the second drug treatment; and wherein the steps of the method are performed in accordance with a processor and a memory.

2. The computer-implemented method of claim 1, further comprising:

receiving biological sample information from the plurality of subjects during the first drug treatment at a third time period;

comparing the biological sample information at the third time period with the biological sample information at the second time period;

generating another precedence graph based on results of the comparison; and determining one or more additional drug treatments based on the other precedence graph.

3. The computer-implemented method of claim 2, further comprising:

receiving biological sample information from the plurality of subjects during the first drug treatment at a fourth time period;

comparing the biological sample information at the fourth time period with the biological sample information at the third time period;

generating another precedence graph based on results of the comparison; and determining one or more additional drug treatments based on the other precedence graph.

4. The computer-implemented method of claim 1, wherein the second drug treatment comprises stopping the second drug treatment.

5. The computer-implemented method of claim 1, wherein the second drug treatment comprises altering the first drug treatment with the one or more other drugs.

6. An article of manufacture comprising a computer-readable storage medium for storing computer-readable program code which, when executed, causes a computer to:

receive, from a biological sample information input module associated with a network, biological sample information comprising genomic information from a plurality of subjects at a first time period, wherein the first time period is before a first drug treatment of cancer;

receive, from the biological sample information input module associated with the network, biological sample information from the plurality of subjects at a second time period, wherein the second time period is during the first drug treatment with one or more drugs;

compare, utilizing a biological sample information comparative analyzer module associated with the network, the biological sample information at the second time period with the biological sample information at the first time period;

generate, from a precedence graph generator module associated with the network, a precedence graph based on results of the comparison, wherein the precedence graph is generated by using frequencies of related pairs from a graph capturing a set of relationships from the comparing to identify those that meet a significance threshold from a given overall distribution of frequencies;

analyze, utilizing the precedence graph generator module associated with the network, the precedence graph to determine if the biological sample information at the second time period comprises genomic alteration information of the biological sample for each of the plurality of subjects;

build, from a model builder module associated with the network, a model based on the analyzing the precedence graph utilizing a machine learning process;

cause to implement, based on a response actuator module associated with the network, a second drug treatment of cancer to one or more given subjects of the plurality of subjects based in part on the model;

compare, utilizing the biological sample information comparative analyzer module associated with the network, biological sample information of a biological sample of another given subject different from the one or more given subjects of the plurality of subjects taken before a third drug treatment of cancer with the model based on analyzing the precedence graph to determine one or more probabilities of development of an alteration of the biological sample of the other given subject different from the one or more given subjects of the plurality of subjects; and based on the one or more probabilities of development of an alteration of the biological sample, cause to implement, based on the response actuator module associated with the network, the third drug treatment to the other given subject that target the alteration;

wherein building, from the model builder module associated with the network, a model based on the analyzing the precedence graph utilizing a machine learning process, further comprises:

storing historical data of past performance for each biological sample information;

storing genomic alterations associated with a given drug treatment different from the first drug treatment, the second drug treatment and the third drug treatment of a particular drug or a drug combination that are potential targets for further drug treatment; and creating a set of identified post-treatment mutational convergences associated with a resistance mechanism in response to the given drug treatment;

wherein causing to implement, based on the response actuator module associated with the network, the second drug treatment to the one or more given subjects of the plurality of subjects based in part on the model comprises identifying one or more other drugs different than the one or more drugs of the first drug treatment to improve response to the second drug treatment and decrease drug resistance in the second drug treatment.

7. The article of manufacture of claim 6, wherein the computer-readable program code which, when executed, further causes a computer to:

receive biological sample information from the plurality of subjects during the first drug treatment at a third time period;

compare the biological sample information at the third time period with the biological sample information at the second time period;

generate another precedence graph based on results of the comparison; and determine one or more additional drug treatments based on the other precedence graph.

8. The article of manufacture of claim 7, wherein the computer-readable program code which, when executed, further causes a computer to:

receive biological sample information from the plurality of subjects during the first drug treatment at a fourth time period;

compare the biological sample information at the fourth time period with the biological sample information at the third time period;

generate another precedence graph based on results of the comparison; and determine one or more additional drug treatments based on the other precedence graph.

9. The article of manufacture of claim 6, wherein the second drug treatment comprises stopping the second drug treatment of.

10. The article of manufacture of claim 6, wherein the second drug treatment comprises altering the first drug treatment with one or more other drugs.

11. A system comprising:
a memory; and
at least one processor operably coupled to the memory and configured for:

receiving, from a biological sample information input module associated with a network, biological sample information comprising genomic information from a plurality of subjects at a first time period, wherein the first time period is before a first drug treatment of cancer, receiving, from the biological sample information input module associated with the network, biological sample information from the plurality of subjects at a second time period, wherein the second time period is during the first drug treatment with one or more drugs;

comparing, utilizing a biological sample information comparative analyzer module associated with the network, the biological sample information at the second time period with the biological sample information at the first time period;

generating, from a precedence graph generator module associated with the network, a precedence graph based on results of the comparison, wherein the precedence graph is generated by using frequencies of related pairs from a graph capturing a set of relationships from the comparing to identify those that meet a significance threshold from a given overall distribution of frequencies;

analyzing, utilizing the precedence graph generator module associated with the network, the precedence graph to determine if the biological sample information at the second time period comprises genomic alteration information of the biological sample for each of the plurality of subjects;

building, from a model builder module associated with the network, a model based on the analyzing the precedence graph utilizing a machine learning process;

causing to implement, based on a response actuator module associated with the network, a second drug treatment of cancer to one or more given subjects of the plurality of subjects based in part on the model;

comparing, utilizing the biological sample information comparative analyzer module associated with the network, biological sample information of a biological sample of another given subject different from the one or more given subjects of the plurality of subjects taken before a third drug treatment of cancer with the model based on analyzing the precedence graph to determine one or more probabilities of development of an alteration of the biological sample of the other given subject different from the one or more given subjects of the plurality of subjects; and based on the one or more probabilities of development of an alteration of the biological sample, causing to implement, based on the response actuator module associated with the network, the third drug treatment to the other given subject that target the alteration;

wherein building, from the model builder module associated with the network, a model based on the analyzing the precedence graph utilizing a machine learning process, further comprises:

storing historical data of past performance for each biological sample information;

storing genomic alterations associated with a given drug treatment different from the first drug treatment, the second drug treatment and the third drug treatment of a particular drug or a drug combination that are potential targets for further drug treatment; and creating a set of identified post-treatment mutational convergences associated with a resistance mechanism in response to the given drug treatment;

wherein causing to implement, based on the response actuator module associated with the network, the second drug treatment to the one or more given subjects of the plurality of subjects based in part on the model comprises identifying one or more other drugs different than the one or more drugs of the first drug treatment to improve response to the second drug treatment and decrease drug resistance in the second drug treatment.

12. The system of claim 11, wherein the at least one processor is further configured for:
   receiving biological sample information from the plurality of subjects during the first drug treatment at a third time period;
   comparing the biological sample information at the third time period with the biological sample information at the second time period;
   generating another precedence graph based on results of the comparison; and
   determining one or more drug treatments based on the precedence graph.

13. The system of claim 12, wherein the at least one processor is further configured for:
   receiving biological sample information from the plurality of subjects during the first drug treatment at a fourth time period;
   comparing the biological sample information at the fourth time period with the biological sample information at the third time period;
   generating another precedence graph based on results of the comparison; and
   determining one or more additional drug treatments based on the other precedence graph.

14. The system of claim 11, wherein the second drug treatment comprises stopping the second drug treatment.

15. The system of claim 11, wherein the second drug treatment comprises altering the first drug treatment with one or more other drugs.

* * * * *